US009489466B2

(12) United States Patent
Costantino et al.

(10) Patent No.: US 9,489,466 B2
(45) Date of Patent: Nov. 8, 2016

(54) TRANSPORTATION AND RESORT INFRASTRUCTURE, AND ASSOCIATED CUTANEOUS INFORMATION DEVICE AND METHOD

(71) Applicants: Peter Costantino, Westport, CT (US); Laurie Costantino, Westport, CT (US); Michael Gilvary, Westport, CT (US); Anthony H. Handal, Westport, CT (US)

(72) Inventors: Peter Costantino, Westport, CT (US); Laurie Costantino, Westport, CT (US); Michael Gilvary, Westport, CT (US); Anthony H. Handal, Westport, CT (US)

(*) Notice: Subject to any disclaimer, the term of this patent is extended or adjusted under 35 U.S.C. 154(b) by 0 days.

(21) Appl. No.: 14/860,646

(22) Filed: Sep. 21, 2015

(65) Prior Publication Data

US 2016/0103925 A1 Apr. 14, 2016

Related U.S. Application Data

(60) Provisional application No. 62/053,725, filed on Sep. 22, 2014.

(51) Int. Cl.

| G06K 7/06 | (2006.01) |
|---|---|
| G06F 17/30 | (2006.01) |
| G06K 19/077 | (2006.01) |
| G06K 19/04 | (2006.01) |
| G06F 19/00 | (2011.01) |
| G06K 7/14 | (2006.01) |
| G06Q 50/12 | (2012.01) |

(52) U.S. Cl.
CPC ....... *G06F 17/30879* (2013.01); *G06F 19/323* (2013.01); *G06K 7/1447* (2013.01); *G06K 19/041* (2013.01); *G06K 19/0776* (2013.01); *G06K 19/07722* (2013.01); *G06K 19/07749* (2013.01); *G06Q 50/12* (2013.01)

(58) Field of Classification Search
CPC .......... G06K 7/06; G06K 7/10; G06K 19/00; G06K 19/06; G06K 15/00; G06F 17/00
USPC ........... 235/441, 375, 462.01, 487, 491, 383
See application file for complete search history.

(56) References Cited

U.S. PATENT DOCUMENTS

| 6,201,662 | B1 | 3/2001 | Graves |
|---|---|---|---|
| 7,758,080 | B1 | 7/2010 | Vilder |
| 7,798,404 | B2 | 9/2010 | Gelbman |
| 8,408,602 | B2 * | 4/2013 | Berson ................. B42D 25/324 235/454 |
| 2003/0183695 | A1 * | 10/2003 | Labrec ................... G06K 19/08 235/487 |
| 2003/0217489 | A1 | 11/2003 | Witkowski |
| 2003/0226897 | A1 * | 12/2003 | Jones ...................... B41M 3/14 235/488 |
| 2004/0091659 | A1 | 5/2004 | Banks |

(Continued)

*Primary Examiner* — Edwyn Labaze
(74) *Attorney, Agent, or Firm* — Handal & Morofsky, LLC

(57) ABSTRACT

Apparatus for identifying and providing for the retrieval of information relating to an individual, comprises an adhesive layer and a machine readable device secured to said adhesive layer. The machine readable device is encoded with identification information. A first quantity of ink deposited on said adhesive layer is arranged to provide a physiologically perceptible and humanly understandable visual indication of information relating to set individual. The adhesive layer, the machine readable device and said first quantity of ink form an individual identification device. The machine readable device is secured to said adhesive layer further comprises a second quantity of ink deposited on said adhesive layer and arranged to provide a machine readable image. A plurality of reader devices and said individual identification device provide information respecting the individual identified by said individual identification device to a computer system which includes a memory with an algorithm for processing collected information.

22 Claims, 12 Drawing Sheets

(56) References Cited

U.S. PATENT DOCUMENTS

| | | |
|---|---|---|
| 2005/0171787 A1 | 8/2005 | Zagami |
| 2006/0031099 A1 | 2/2006 | Vitello |
| 2006/0037502 A1* | 2/2006 | Warther ........... G06K 19/06028 |
| | | 101/232 |
| 2006/0248767 A1 | 11/2006 | Hofer |
| 2007/0029377 A1 | 2/2007 | Hinckley |
| 2008/0208236 A1 | 8/2008 | Hobbs |
| 2008/0275327 A1 | 11/2008 | Faarbaek |
| 2010/0271180 A1 | 10/2010 | Oberle |
| 2011/0081522 A1 | 4/2011 | Kim |
| 2011/0096388 A1 | 4/2011 | Agrawal |
| 2011/0303344 A1 | 12/2011 | Bortel |
| 2013/0149508 A1 | 6/2013 | Kwak |
| 2014/0008441 A1* | 1/2014 | Huynh ................. G09F 3/0294 |
| | | 235/468 |
| 2014/0035720 A1* | 2/2014 | Chapman ........... G07C 9/00031 |
| | | 340/5.51 |
| 2015/0053759 A1 | 2/2015 | Cahill, Jr. |

* cited by examiner

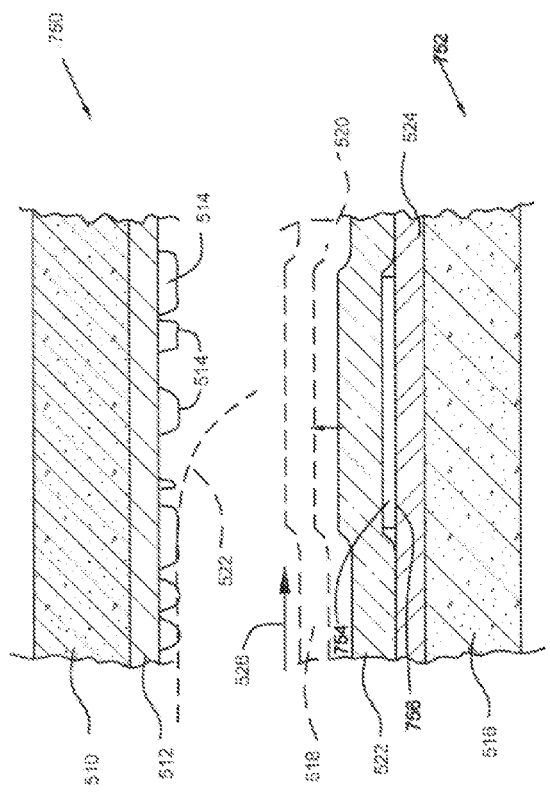
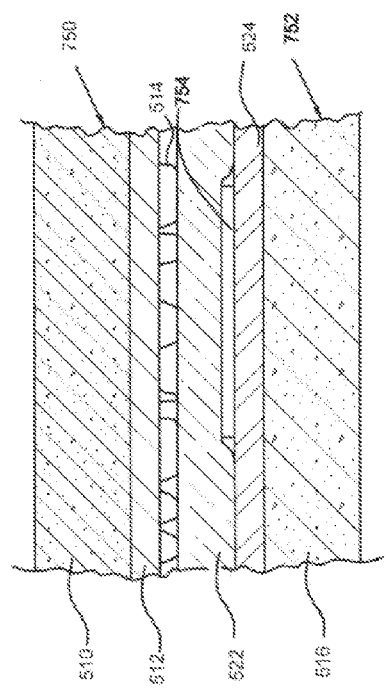
Figure 11
Figure 12

TRANSPORTATION AND RESORT INFRASTRUCTURE, AND ASSOCIATED CUTANEOUS INFORMATION DEVICE AND METHOD

CROSS REFERENCE TO RELATED APPLICATIONS

This application claims the benefit of Provisional Patent Application No. 62/053,725, filed Sep. 22, 2014, the disclosure of which are hereby incorporated herein by reference.

STATEMENT REGARDING FEDERALLY SPONSORED RESEARCH OR DEVELOPMENT (Not applicable)

TECHNICAL FIELD

The invention relates to apparatus and methods for tracking for the purposes of the security, safety, billing and other servicing of patrons at travel and recreational facilities, such as an airline terminal, resort, convention center or hotel.

BACKGROUND OF THE INVENTION

Resorts, country clubs, municipal recreational facilities, cruise ships, convention centers, theme parks, museums and so forth often have many recreational options. Such options may include theatrical presentations, rides, restaurants, fast food facilities, classes, parties, meetings, exhibition halls, pools, tennis courts, horseback riding, and so forth. Operators of such facilities often have a number of reasons for controlling and/or monitoring use of and or access to their facilities, and the various attractions located therein by patrons.

At the present time, in a typical facility, one or more individuals are present at the entrance to the venue hosting the attraction, event or other offering. These individuals check persons wishing to enter the attraction venue, requesting and/or collecting and/or ripping tickets in half.

Tickets to facilities, such as amusement parks, are often purchased on the Internet. However, due to the fact that multiple tickets can be printed, consumers are generally provided only with an identification number or alphanumeric. When the individual arrives at the attraction, he or she presents the reservation number at a kiosk where specially printed tickets are provided. Typically these tickets are collected and ripped in half at the venue. These specially printed tickets have a format which is largely unknown to the individual attending and offering and which may be difficult to copy.

Such systems suffer from multiple drawbacks. For example, the cost of personnel at the entrance to the venue is high. Moreover, for quality of service reasons, multiple personnel are often employed at the entrance to the venue. In addition, the possibility exists that reservations may be made and resold by "scalpers". Individuals may even swap tickets once they enter the facility, posing a security risk. Likewise, numerous security risks are presented at an airport terminal and aboard aircraft.

Given the longstanding recognition that it is desirable to track usage at a facility, for many years numerous solutions have been proposed and implemented. For example, using a rubber stamp and ink to identify individuals who have paid a fee is something which has been done for at least 50 years. Other possibilities may involve selling tickets for cash, providing unlimited access to all facilities, for example in a convention center, or other expedient. The possibility also exists to use RFID technology which has been used in a wide variety of venues, such as transit systems. However, tickets, RFID identifiers, and the like have the disadvantage that they can be transferred to other persons. Moreover, in the case of tickets or RFID identifier devices associated with unlimited use, a single one of the same may be shared by multiple individuals, one of whom is using the ticket while the other is perhaps traveling to town, and then vice versa, reducing the income of the facility operator, and or posing a security risk.

Despite their drawbacks and limitations, tickets and rubberstamps applied to the skin of the user remain the only significant methodologies used for identification of individuals.

SUMMARY OF THE INVENTION

In accordance with the invention, a method and a temporary cutaneous identification device for identifying individuals is provided.

In accordance with one embodiment of the invention, the temporary cutaneous identification device includes a barcode which may be read by or at, for example, the turnstile providing admission to an attraction venue. Alternatively, the inventive temporary cutaneous identification device may be read by a smartphone being used by a member of the facility's staff. In such instance, the smartphone used by the staff member has an appropriate application downloaded on it, which provides for both 1) the input of data associated or to be associated with the individual's temporary cutaneous identification device, and 2) the retrieval of information either by direct request or keyword searching. This enables the generation of a more complete guest record at a central server. At the same time, artificial intelligence software on a computing device with the capability of accessing the central server database periodically checks guest conditions, measurements, medications, procedures and so forth to identify potential issues, inconsistencies, and other circumstances suitable for bringing to the attention of different classes of resort personnel. More particularly, it is contemplated that certain conditions might be brought to emergency services, security or other personnel.

The inductive for identifying and providing for the retrieval of information relating to an individual comprises an adhesive layer and a machine readable device secured to said adhesive layer. The machine readable device is encoded with identification information. A first quantity of ink deposited on said adhesive layer is arranged to provide a physiologically perceptible and humanly understandable visual indication of information relating to set individual. The adhesive layer, the machine readable device and said first quantity of ink form an individual identification device. The machine readable device is secured to said adhesive layer further comprises a second quantity of ink deposited on said adhesive layer and arranged to provide a machine readable image. A plurality of reader devices and said individual identification device provide information respecting the individual identified by said individual identification device to a computer system which includes a memory with an algorithm for processing collected information.

BRIEF DESCRIPTION OF THE DRAWINGS

The operation of the inventive infrastructure and method will become apparent from the following description taken in conjunction with the drawings, in which:

FIGS. 11-14 illustrates an RFID embodiment of the inventive badge;

DETAILED DESCRIPTION OF THE PREFERRED EMBODIMENTS

Figure 1:
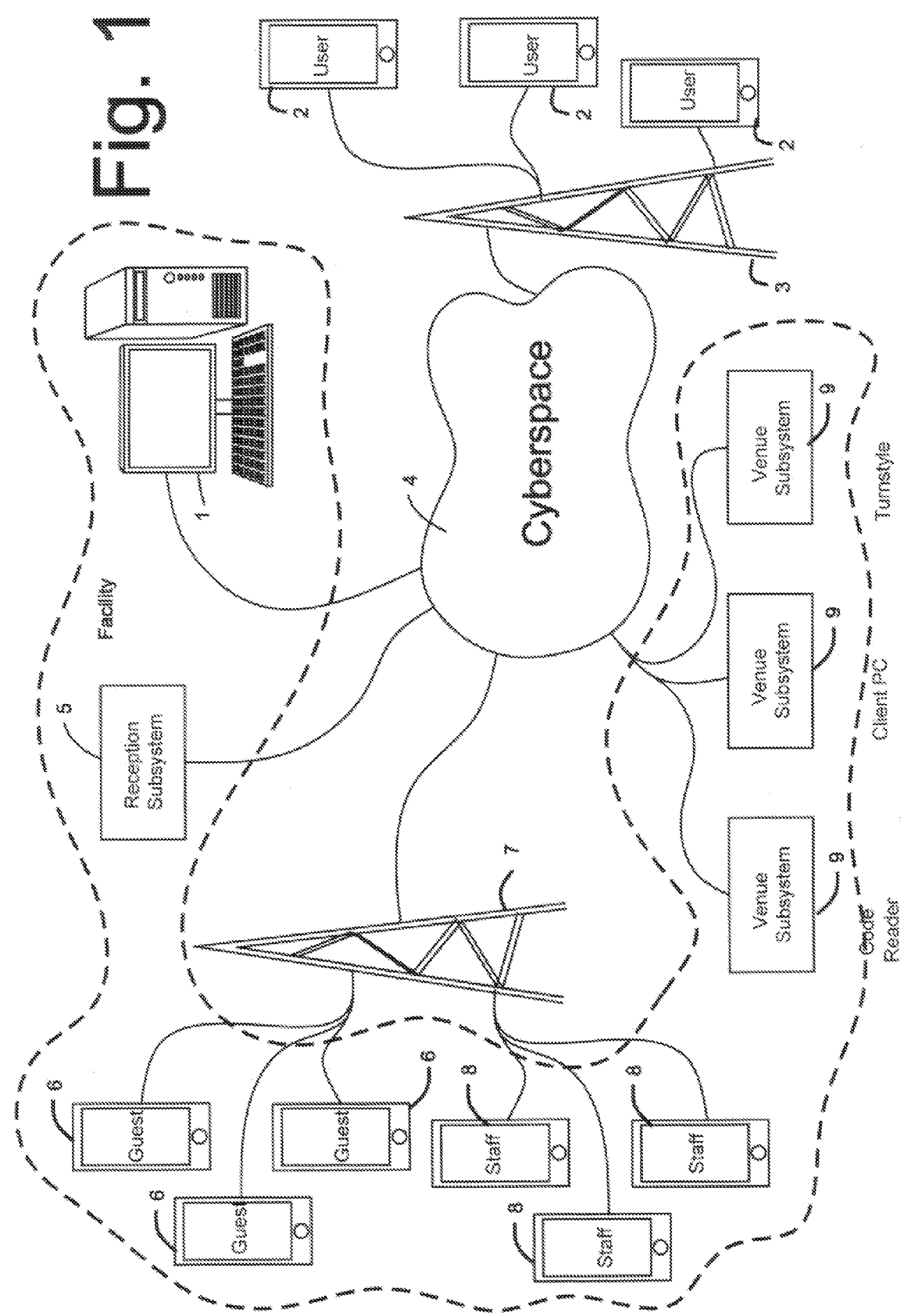
FIG. 1 is a block diagram generally illustrating a general implementation of the present invention.

A hardware system constructed in accordance with the present invention and suitable for practicing the method of the present invention is illustrated in FIG. 1. Generally, in accordance with the invention, the inventive method is initiated by users communicating with the facility server 1 through, for example, a plurality of Internet connected computers, or, as illustrated, cellular smartphones 2. Cellular smartphones 2 are connected, via cell towers 3 and cyberspace 4, to server 1.

In the accordance with the invention as illustrated, a user connects to the facility (such as a resort, convention center or theater) by accessing the facility website and reserving one or a number of facility products, such as a room, a ticket for a ride, a ticket for a party, access to an ice skating rink or ski lift (for example for a morning, day or week), access to a pool or tennis court, access to a convention hall, access to a course, a ticket for a theater, etc.

Such selections as well as user information may be downloaded from user devices 2 to server 1 where it may be stored for later use. At the same time the individual will provide, optionally, credit card information, identification information, demographic information, etc. The individual may also be asked whether he wants to preserve certain nights, movies, attractions, meetings, and so forth. All of this information may be stored on server 1 for later use. The guest may also be given the opportunity to select a level of membership at the facility, such as bronze, silver, gold and platinum levels of membership. Each level of membership would have different privileges and different access to the various attractions at the facility.

When the user-guest arrives at the facility, a reception subsystem 5 (which may be a programmable general-purpose personal computer) recalls stored information and the user-guest is given the opportunity to change rights (for example by raising or lowering his level of membership), movies, or other attractions.

At reception, the user is provided with the inventive cutaneous identification device, which confers upon the user the ability to access attractions as a guest (at a particular level), and is thus free to enjoy the attractions of the facility. The guest may continue to use his personal smartphone 6, which can access server 1 via local cell towers 7 and cyberspace 4 for the purpose of implementing new choices, or being accessed by the system on matters related to the stay of the guest. Such use by guests after they are at the facility may involve making additional reservations, receiving alerts, receiving offers, responding to offers, changing their preselected options, and so forth, all of which may be done by accessing server 1. Likewise, staff members may use their personal smartphones 8, to receive instructions to assist certain customers. Staff members may also use their smartphones 8 to make changes or otherwise assist guests.

In accordance with the invention, guest smart phones 6 may be used to track location, which information is useful, for example, for the purpose of making offers or for security purposes. Such tracking may be done after users consent, using the publicly available cellular telephone system.

Alternatively, while at the facility, users may be given option to sign onto the Wi-Fi system for the facility, and thus avoid use of their cellular time and data. In the event that the user is on the facility's private Wi-Fi network, the private Wi-Fi network of the facility may also be used to determine the location of the user.

In accordance with the invention, access to various attractions, such as tennis courts, pools, theaters and so forth may be gated, with gates responsive to the inventive cutaneous information system to provide admission. For example, venues 9 may be provided with turnstiles, and when the user presents his cutaneous identification device to a scanner (for example by holding the wrist in facing relationship to a scanner), the turnstile is released and admission is allowed.

Alternatively or additionally, staff smartphones 8 may be provided with a scanner app, which allows them to read the inventive cutaneous identification device, and allow those with proper credentials into the attraction, or take steps to validate the individual to enter the attraction, for example, by charging their account with the cost of admission to the attraction. Accordingly, it will be understood that server 1, reception subsystem computer 5, guest smart phones 6, staff smartphones 8 and venue subsystems 9 together cooperate, through the use of cyberspace 4 and cellular tower 7, to comprise the facility's system.

Figure 2:
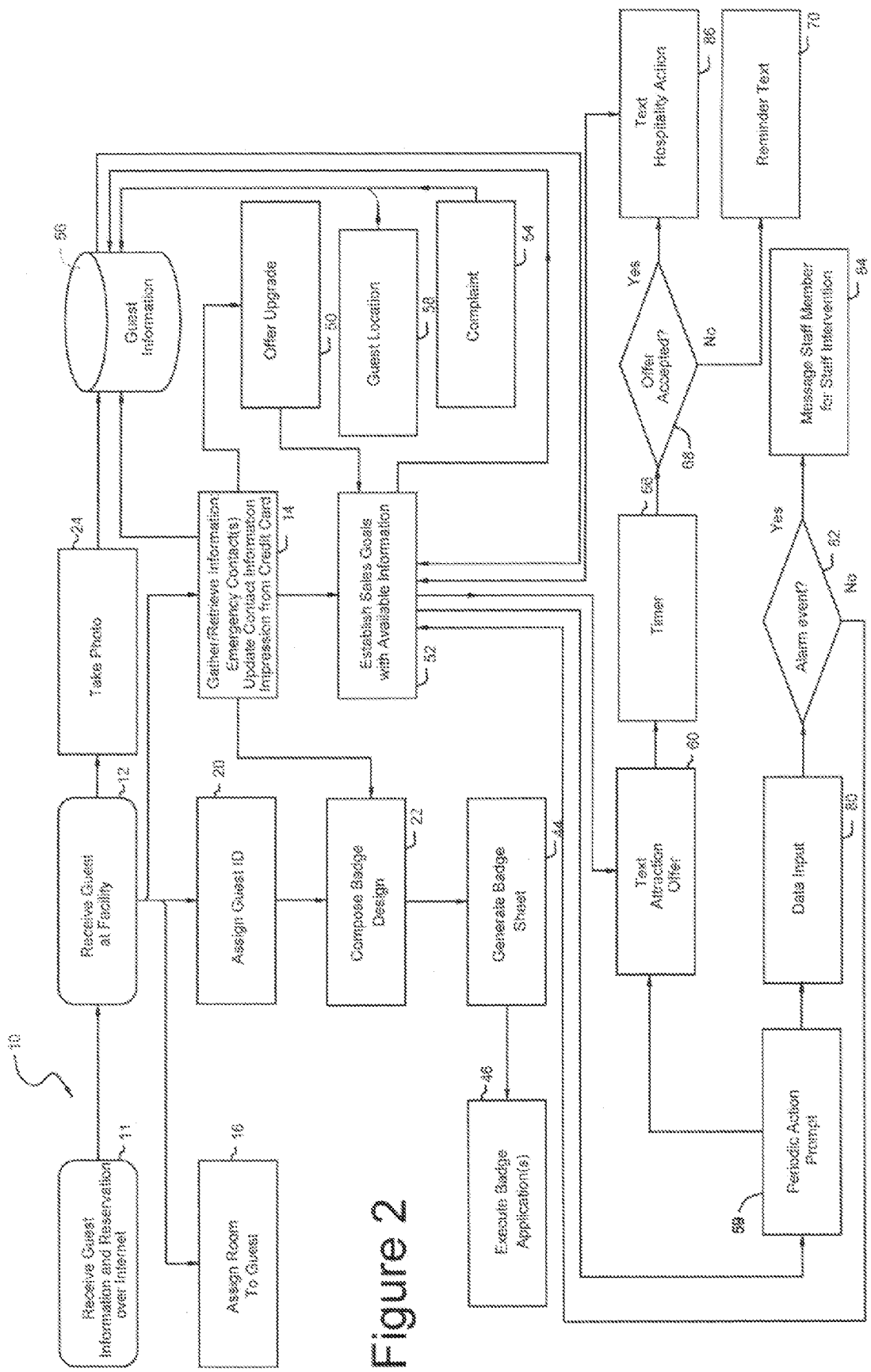
FIG. 2 is a flowchart illustrating an exemplary embodiment of the method as implemented according to the present invention.

Turning to FIG. 2, the method 10 of the present invention may be understood. Initially, guest information was previously stored at step 11 on the hard drive of server 1, when a guest made his or her reservation. After the guest checks in at step 12, guest information is retrieved at step 14. Additional information may also be gathered at step 14 and may include information of the type not normally collected over the Internet, such as emergency contact information, changes in information since the reservation was made, the taking of an impression of the credit card or the electronic equivalent thereof, and so forth. Such information is stored on the hard drive 56 of server 1.

In accordance of the invention, the option is provided for personalized treatment of the individual. For example, information on such things as allergies, food preferences, recreational interests, and so forth may be gathered at the reception desk and input into server 1. At step 16 the guest is given his room, and at step 20 an identification number (or alphanumeric) associated with the guest at the time of the booking of the reservation over, for example, the Internet is associated with information that the individual is now a guest. In accordance with one embodiment are of the invention, this information may be sent to a publicly accessible database. Moreover, in the event that the airline ticket and resort stay are booked together, in accordance with the invention, such information is available at the airport when the individual or group of individuals is entering the airport for the purpose of flying to the resort, and may be used to improve security, as detailed below. The inventive temporary cutaneous identification device is then composed at step 22 based on information stored in hard drive 56 at step 14. Optionally, a guest is given a choice of designs, or the design may be a barcode or similar identifier printed in invisible ink, that is ink visible only under the ultraviolet light of a scanner located at the venue, for example at the entrance, of the particular attraction.

Figure 3:
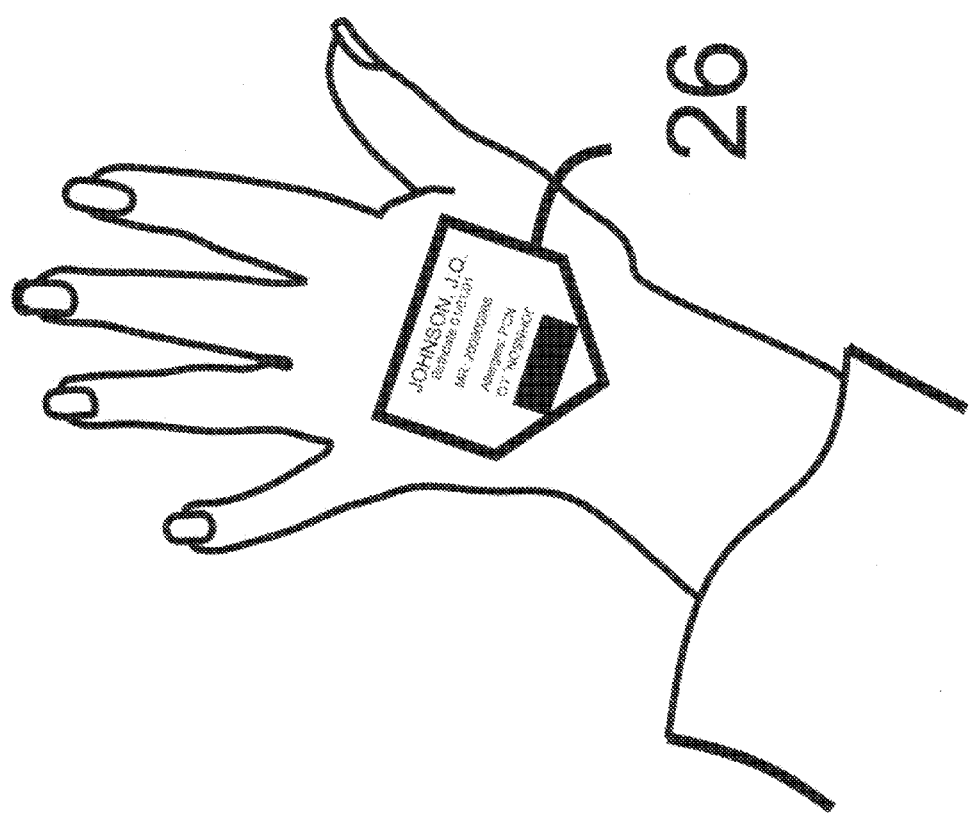
FIG. 3 illustrates an applied identifier or badge according to the present invention.

The inventive cutaneous identification device is then printed at step 44 and applied by, for example, hotel personnel in the reception area of the hotel, to the back of the wrist or the back of the hand, for example, of the guest at step 46. The application of a badge 26 to the back of the hand is illustrated in FIG. 3. Alternatively, if the individual has received an inventive cutaneous identification device at the airport, the same device may continue to be used as long as it has not deteriorated to the point where use becomes erratic.

In accordance with one embodiment of the invention, guest badges for all guests in the system will include the same types of information in the same places. The optimal size for the inventive temporary identification device (hereinafter referred to as "badges" or "devices") is approximately equal to between 15% and 35% of the circumference of the wrist. Based on gender identification in the database, larger size badges may be provided for men as opposed to women, and smaller devices may be provided for children in accordance with their age, as the same is recorded in the database of server 1.

In accordance with one embodiment of the invention, diecut sheets, similar to the sheets used with printers making temporary tattoos, may be used to print the badges. Different diecut sheets may be provided for guest badges of different sizes, for example in the case of a family.

Figure 4:
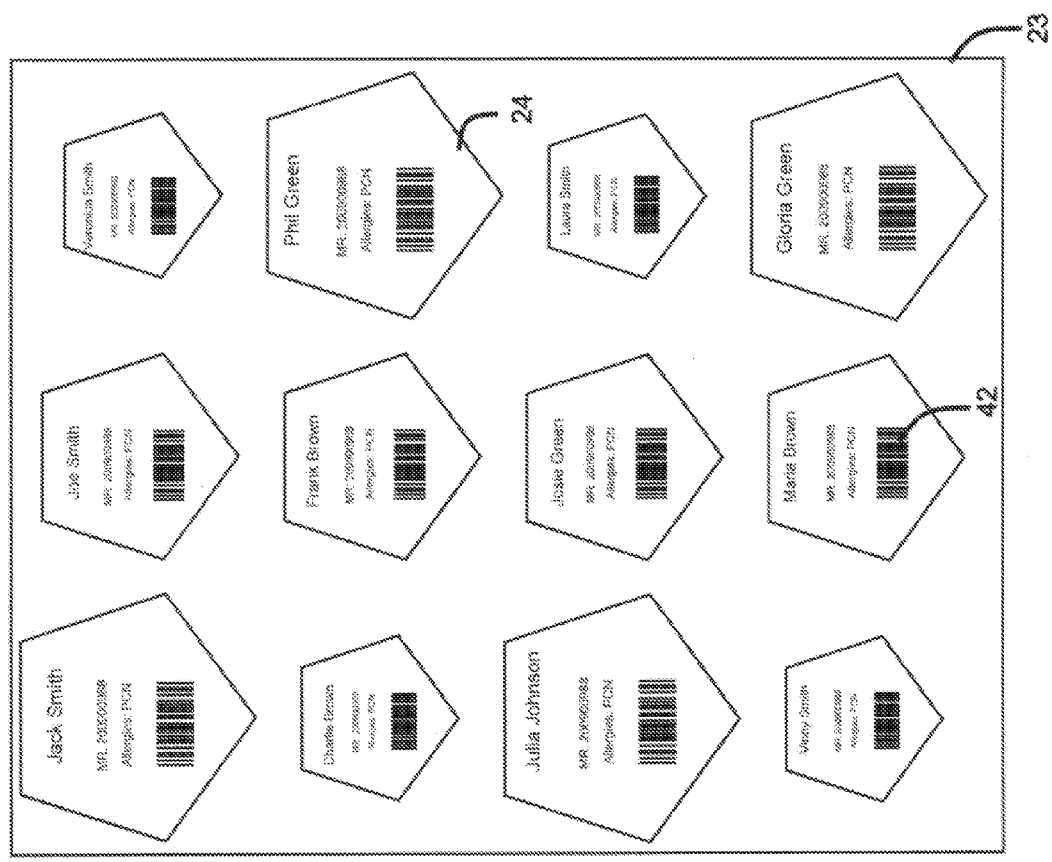
FIG. 4 illustrates a sheet printed with identifiers, in this case for a group of individuals, as implemented according to the present invention.

In accordance with the invention, it is contemplated that a plurality of guest badges will be generated at the same time in the printing of a single sheet, for example for a family or larger party, on a single sheet of, for example, paper 23, as illustrated in FIG. 4. In this figure, guest badges 24 are scaled to different sized members of a family or group. In accordance with one embodiment of the invention, it is contemplated that piezoelectric inkjet technology is used to generate sheets containing the inventive badges. This allows a wide variety of printing inks, such as the FDA approved inks produced by Colorcon, which are preferred in accordance with the invention.

In accordance with the invention, the guest badge preferably includes an optically readable code 42. Alternatively, optically readable code 42 may be replaced by any automated readable device, such as an RFID chip, a quad code, and so forth. Moreover, it is noted that the system may accommodate OCR capability which would make the generation of a machine-readable code, such as code 42, unnecessary, because the system could simply read the same information that a human operator reads.

In accordance with the invention, guest badges are generated using technology of the types used to generate temporary tattoos. Thus, the guest badges essentially comprise an adhesive layer with an image formed of an ink deposit overlying the adhesive layer. After application, the result is an ink image glued to the skin by the adhesive.

Referring back to FIG. 2, at step 24 a camera connected to reception subsystem 5 takes a picture of the guests at the reception area. This photo is then stored on hard drive 56.

At step 50, available information is analyzed by the system in accordance with an algorithm and, if appropriate, the system instructs the individual receiving the guest to offer an upgrade at step 50. The system then proceeds to step 52 where sales goals are developed by an algorithm on the hard drive, for example, of the server, on the basis of available information. Such sales goals may include overall dollar amounts, and particular items which information indicates as likely to be of interest to the particular guest. Depending upon guest location and, optionally, other factors, particular items (such as products or services, events and so forth) may be suggested to guests by sending them text messages on guest cell phones 6, at step 60. Such suggestions are sent periodically, for example once every 90 minutes during the day and early evening in response to a periodic prompt at step 59.

At a time measured at step 66, the system determines at step 68 whether there has been a response to the text message (for example, acceptance of an invitation to go to a particular attraction close to the location where the guest is at the time of the text message). Location is measured periodically at step 56 using any one of a number of available technologies. If there has been no response after the time has elapsed, the system proceeds to send a reminder text at step 70. Alternatively, if an affirmative response has been received, the system sends a text message to a staff member's smart phone 8 at step 86. The text instructs a staff member to greet the guests and acknowledge the recent decision to accept an invitation to an unscheduled event. A "thank you" gift (such as a free ticket), as determined by the system algorithm at step 52, may also be included as an incentive to accept future invitations. In addition, the system at step 86 sends the acceptance information to database 56 enabling better responses to guest activities and reshaping goals at step 52.

Periodically, in response to prompting at step 59, the system checks, at step 80, data which has been input into the system to determine whether an alarm condition exists. An alarm condition may be indicated by a complaint which the consumer application downloaded by the guest when he arrives at the facility may facilitate by a communication from the guests to server 1 at step 54. If an alarm condition is found to exist, at step 82 the system proceeds to step 84 where text messages sent to the smart phone of a staff member located proximate the guests. Alternatively, if there is no alarm the system proceeds to step 52 where information is updated and goals are reset.

Figure 5:
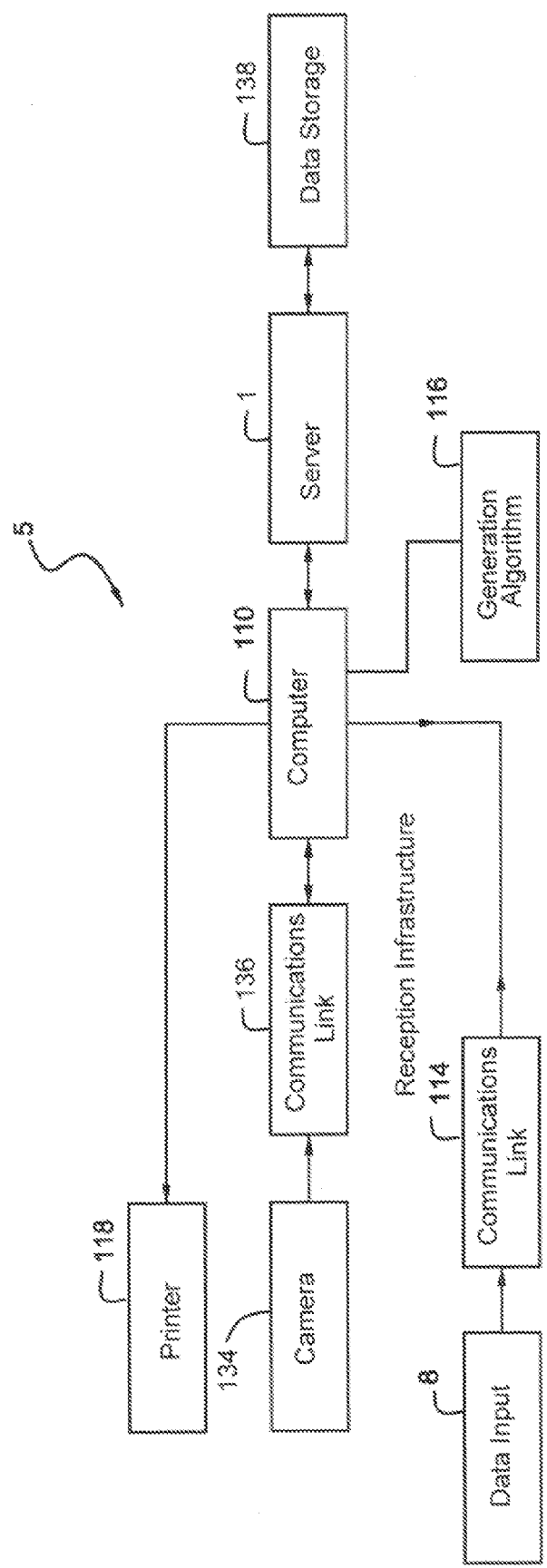
FIG. 5 illustrates in block diagram form the infrastructure of reception hardware in accordance with the present invention.

Referring to FIG. 5, an exemplary embodiment of the reception subsystem is illustrated. Typically subsystem 5 would be located in the reception area of the facility, for example in the case of a hotel, the hotel lobby. In the case of an amusement park, it would be at the kiosk located at the entrance to the facility. Subsystem 5 centers on a computer 110. Computer 110 may receive data input from any suitable data input device such as a keyboard or a wireless input device. For example, data input may be received by one of the smartphones 8 of a staff member and input through any suitable communications link 114, such as the cellular telephone system or a Wi-Fi system, into computer 110. This allows facilities, instead of having a rigid fixed kiosk or similar arrangement, to have a flexible reception arrangement channeling manpower toward reception when that is needed and reallocating its people when circumstances suggest same.

When a guest is being received, the information is communicated to computer 110, which causes computer 110 to consult a generation algorithm 116, which generates the badge design. The badge design is then communicated to and printed by a printer 118, optionally using information stored on the hard drive 138 of server 1. Once printed, the inventive badge may be applied to the back of the hand or wrist or other area on the exposed skin of the guest.

In accordance with the invention, it is also contemplated that a photo of the guest is taken using a camera 134. Camera 134 may be a conventional camera coupled to computer 110 by a cable. Alternatively, camera 134 may be the camera on the smartphone 8 of a staff member and coupled by a cellular communications link 136 to computer 110. Alternatively, dedicated devices operating on a local private wireless network operated by the facility may be employed.

Figure 6:
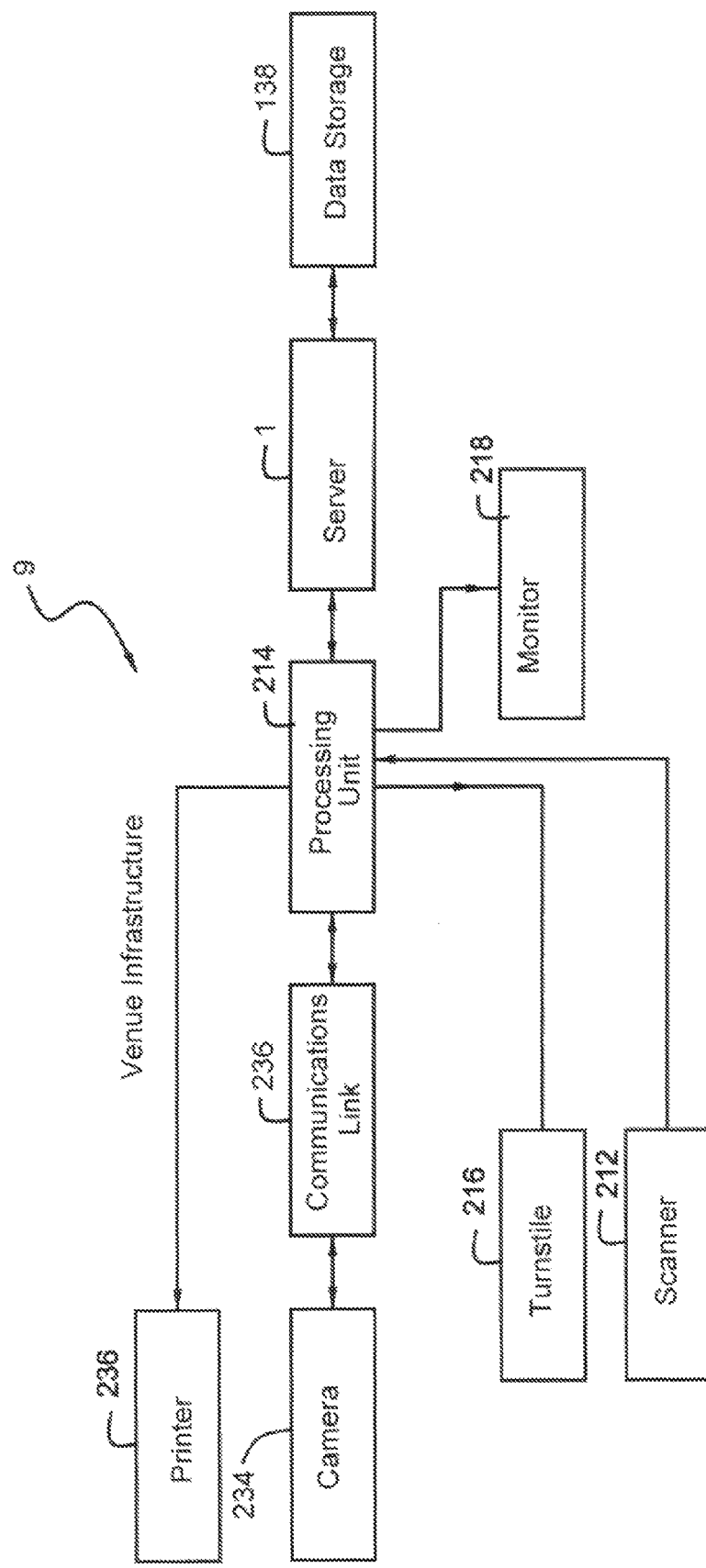
FIG. 6 illustrates in block diagram form the infrastructure of venue hardware in accordance with the present invention.

The structure of venue subsystem 9 is illustrated in FIG. 6. When a person appears at a venue, such as a pool, theater, restaurant and so forth, the guest presents his wrist, for example, to a scanner 212 coupled to a local processing unit, such as a microprocessor or appropriately programmed general purpose computer 214. This causes processing unit 214 to open turnstile 216. The system may also include a monitor 218 to provide instructions to the guest, such as an instruction to present the badge for a second scan if the first scan did not work. Alternatively, or in addition, an audio source may be used to play a message which may be prerecorded or digitally synthesized. Such systems including a scanner, a turnstile, a video monitor, a camera (as discussed below) and an audio source may be used at any point in the system of any of the embodiments where access is to be controlled, whether or not such point is manned by personnel.

If there is a question of guest identity, a camera, permanently connected to processing unit 214 may be used to check guest identity based, for example, on facial recognition. Alternatively, as illustrated, a camera 234 on a smartphone belonging to a staff member or the guest may be coupled by any appropriate communications link 236 to processing unit 214.

In the event that the inventive guest badge has deteriorated to the point where recognition is not reliable, the monitor 218 may present a message that the guest needs a new badge. At the same time, it will send text or other notification to a nearby staff member who will instruct processing unit 214 to create a badge using printer 236. The badge is then applied by the staff member to the wrist of the user after the previous badge has been removed, for example, removed using mineral oil or a specialized product. It is noted that in accordance with the invention, each guest is given a single badge at the time he or she is received at the facility. This is to prevent the use of additional badges by unauthorized persons. Accordingly, replacement badges are applied by facility personnel as the need arises, or as requested by guests.

In accordance with the invention, it is contemplated that the guest admission area of the facility may optionally have on hand a number of input devices, which may take the form of a mini tablet, or full size tablet incorporating a camera and wireless conductivity. When a guest is being received, an input device is given to the guest. The input device prompts the guest to fill in various informational units to be used by the system. This information, including an image of the face of the guest, is directly transferred by the system for storage by the server.

Further in accordance with the invention, it is contemplated that guest image presentations may advantageously also be included on sheets of guest badges.

Figure 7:
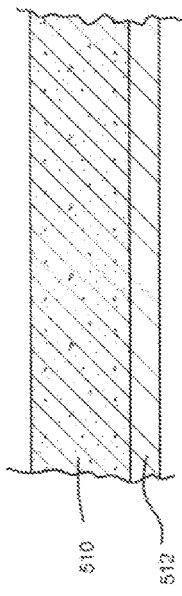
FIG. 7 illustrates a sheet of paper for receiving a temporary cutaneous identification device.

Referring to FIG. 7, a sheet of paper 510 for receiving a temporary cutaneous identification device image is illustrated. As discussed above, the same essentially incorporates temporary tattoo technology and is thus has the advantage of being readily and economically available. Sheet 510 bears a release coating 512.

Figure 8:
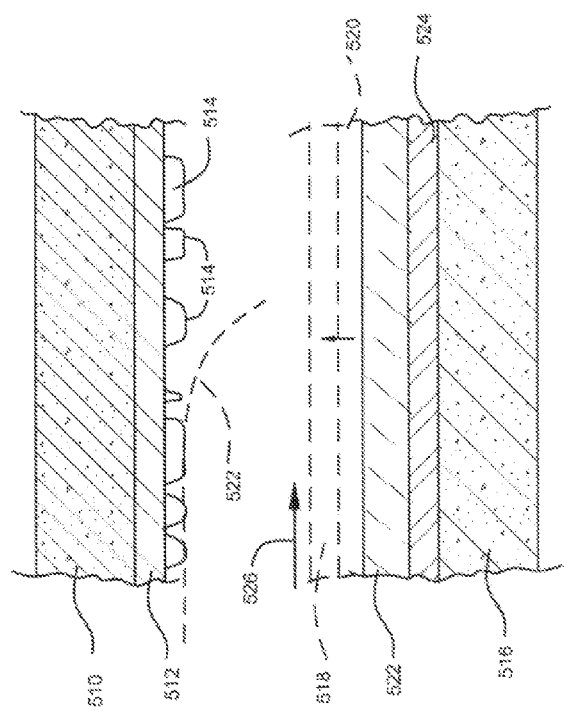
FIG. 8 illustrates components for application of the inventive identification badge.

When it is desired to make a sheet of guest badges, sheet 510 with coating 512 is placed in a laser or inkjet printer and an image is deposited thereon. The image takes the form of deposits of ink 514, as illustrated in FIG. 8. Ink 514 is deposited on and adheres to release coating 512.

Figure 9:
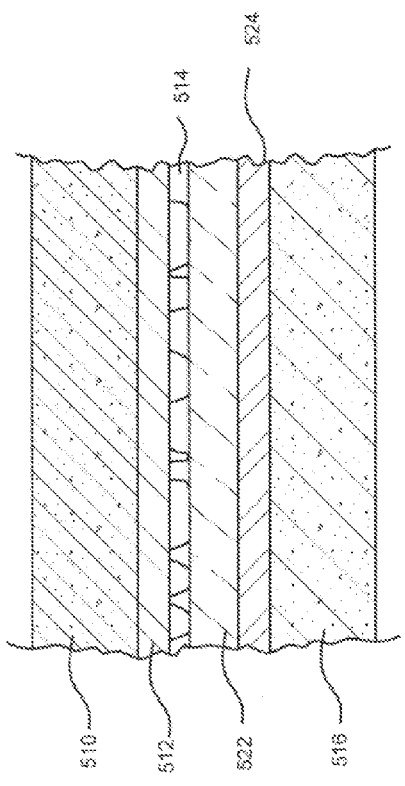
FIG. 9 illustrates a structure that results when one sheet with coating that has ink deposits comes in contact with an exposed adhesive layer of another sheet once a protective layer is taken off.

During the manufacture of a guest badge sheet, a second sheet of paper 516 is put proximate to and in facing spaced relationship to sheet 510 after a protective layer of paper 518 bearing a layer of release agent 520 has been removed. This allows a layer of adhesive 522 overlying a layer of release agent 524 to be exposed prior to assembly of the guest badge sheet, as illustrated in FIG. 9. In accordance with known techniques for the assembly of temporary tattoos, sheet 516 with exposed adhesive layer 522 disposed on it is curled as indicated in phantom lines adjacent ink 514. Sheet 516 is then adhered to one edge of sheet 510, and the curled surface of adhesive 522 is advanced in the direction of arrow 526 as illustrated in FIG. 8. The resulting structure is illustrated in FIG. 9.

Figure 10:
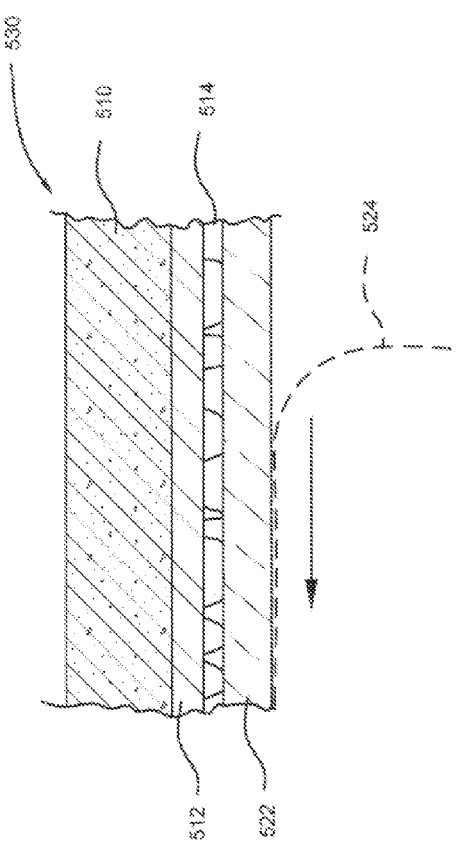
FIG. 10 illustrates a patient badge with a partially removed release layer.

When it is desired to apply a guest badge, a guest badge is separated from the sheet, for example by removing it from the sheet. To apply the guest badge, adhesive layer 522 must be exposed by removal of paper sheet 516 with release layer 524 by peeling the same way as illustrated in FIG. 10. The separated guest badge 530 may then be adhered to the skin of the guest in the manner of a temporary tattoo of conventional design.

After separated guest badge 530 has been adhered to the skin, it is possible to remove paper member 510 with release coating 512 because adhesive 522, transferred from sheet 516 to sheet 510, holds ink 514 more securely than release layer 512. This leaves adhesive 522 secured to the skin and ink 514 forming the desired guest badge image secured by adhesive 522 to the skin of the guest.

The manufacture of badge sheets is of relatively simple methodology. Accordingly, it is contemplated that such manufacture will occur both at the point of admission of the guest (or other point of first application and points of subsequent application) and at the point of use, for example the point of care in the context of a hospital system as described below. Any structure and method of manufacture of the type used in the field of temporary tattoos may be employed to implement the methodology of the present invention.

As discussed above, badges may be manufactured in any facility, such as a hotel or amusement park, by staff using materials commonly available for tattoo generation. Generally, as illustrated in FIG. 11, image receiving sheet 750 made of paper 510 with a release coating 512 is printed with laser or inkjet type ink deposits 514. Image bearing sheet 750 then transfers the ink only to an adhesive sheet 752 by being put into contact with its adhesive layer 522.

In contrast to the optical readable badge previously described, an RFID chip 754 may be employed (either alternatively or in addition to the optically readable badge), as illustrated in FIG. 12. Chip 754 may be an active RFID chip, a passive RFID chip, or any other device capable of acting as a transponder. While passive ISAM band chips operating in the 865-868 MHz range in Europe and the 902-928 MHz range in North America are preferred because of their low cost, typically in the range of $0.15 each, other technologies may be used, including active devices, devices operating in the 3 to 10 GHz range, devices acting in lower microwave frequency ranges, UHF devices of the type operating in the range of about 433 MHz, as well as high-frequency and low-frequency devices. Choice depends upon cost, range desired, and data speed required. However, in accordance with the invention, relatively slow data speeds will provide substantially acceptable functionality for the system described herein.

Figure 13:
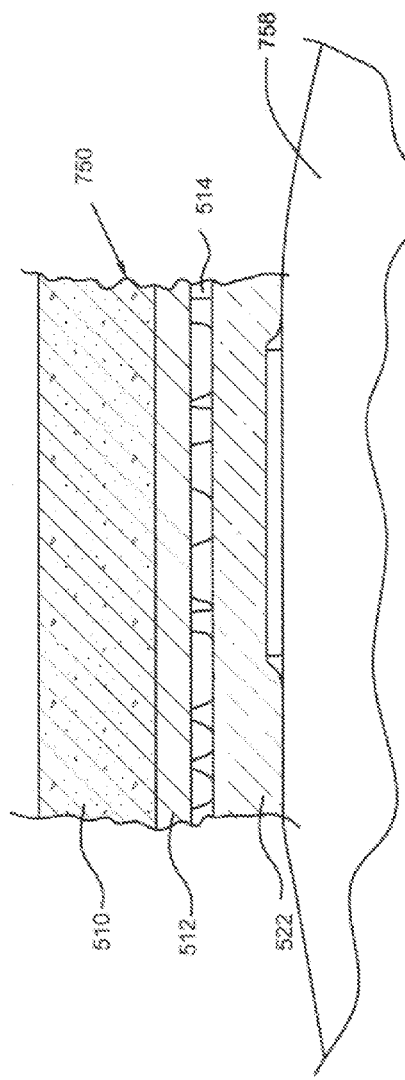
Figure 14:
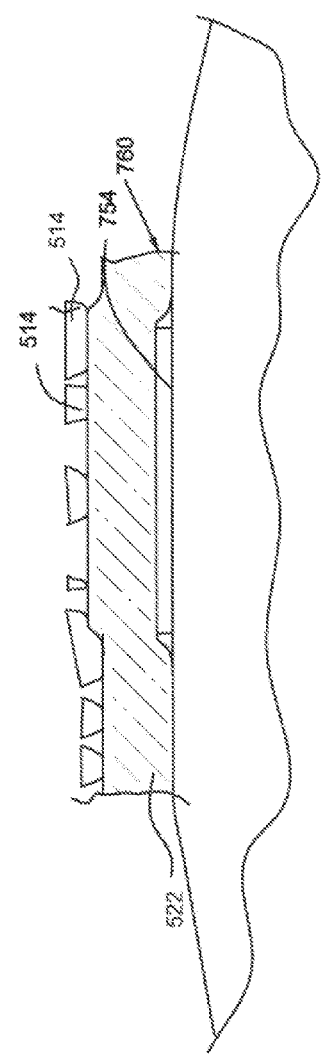

As illustrated in FIG. 11, image bearing sheet 750 is brought into contact with adhesive bearing sheet 752, with adhesive 522 contacting image ink 514, as shown in FIG. 12. Sheets 750 and 752 are then pulled apart resulting in a transfer of the image ink 514 to adhesive layer 522. This arrangement is shown in FIG. 13. In accordance with a preferred embodiment, a quantity of adhesive is deposited on the underside 756 of RFID chip 754, as illustrated in FIG. 11. This facilitates adhesion of the assembly of sheet 752 to skin 758 of a guest. The finished badge applied to the skin is illustrated in FIG. 14.

Such guest badges may be removed by any technique used for the removal of temporary tattoos, such as rubbing with mineral oil, alcohol and so forth.

Moisture may then be applied to paper layer 510, resulting in the release of the assembly of paper layer 510 and release coating 512 from the badge assembly, leaving behind guest badge 760. The resulting badge is shown in FIG. 14.

In accordance with a preferred embodiment, guest badges are applied using a "peel packed" water impregnated foam pad designed to cover the temporary cutaneous identification device fully, and with sufficient aqueous solution that several temporary cutaneous identification devices can be applied with a single pad, but without so much aqueous phase as to drip or run. Such wet sponges, pads or the like may be packaged in any suitable container, such as double foil heat sealed containers of the type used to contain perfumes, condiments, and so forth.

The inventive guest identification badge can also be easily removed using a "peel pack" foam sponge impregnated with a solution capable of dissolving the adhesive of the inventive temporary cutaneous identification device without irritating the skin (e.g., mineral oil, baby oil, Detatchol™, etc.).

Figure 15:
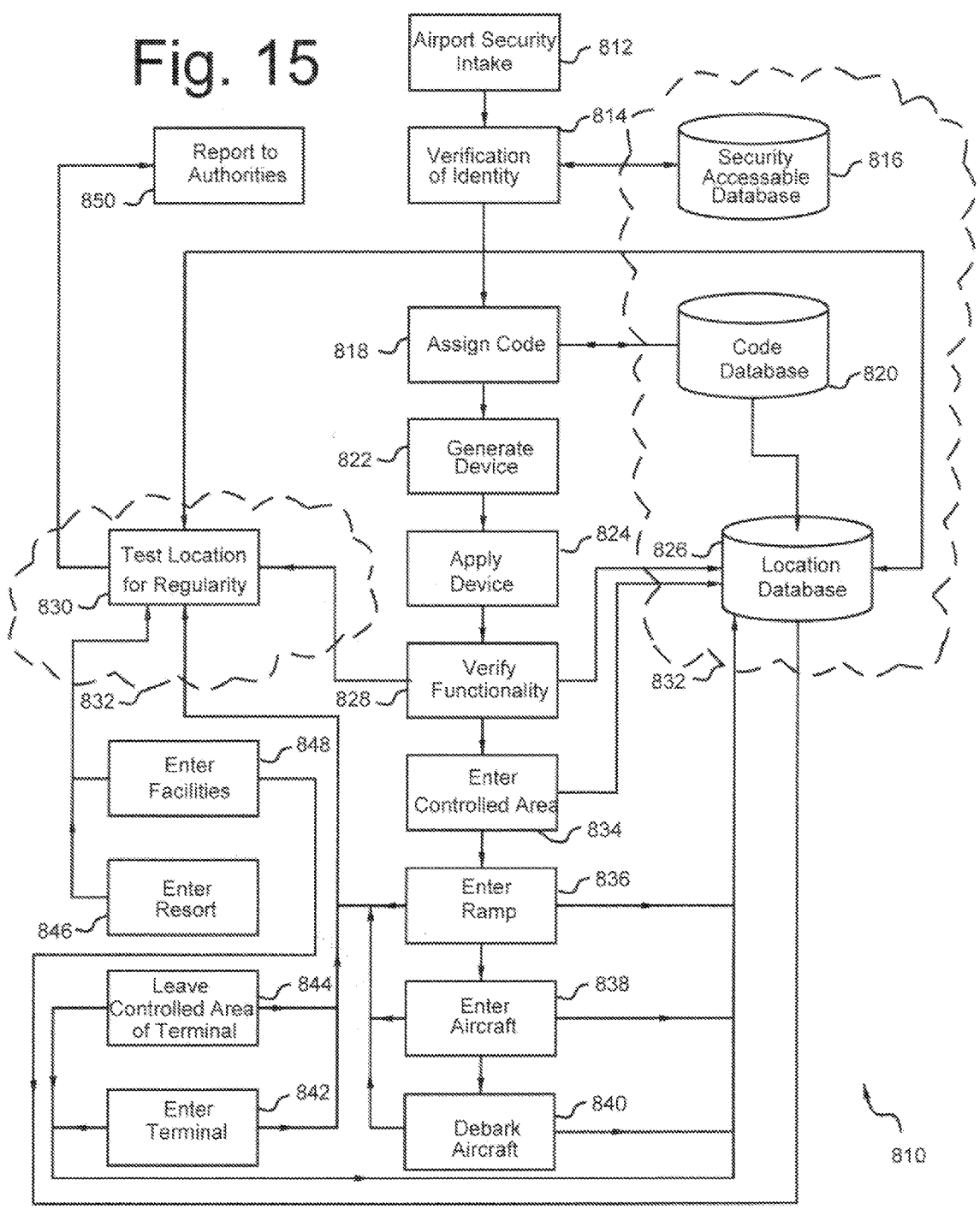
FIG. 15 illustrates the inventive method in a system incorporating travel security, for example in an air travel system.

Referring to FIG. 15, an embodiment of a method 810 in accordance with the invention and particularly useful in connection with implementing security in an airport terminal and in aircraft, and capable of integrated treatment of security, billing, admission and related functions as discussed above in connection with the embodiment of FIGS. 1-14 is shown. Generally, all control, databasing, assignment, messaging an other functions are desirably but optionally performed by a central processing unit with which all information gathering, information presenting and monitoring units communicate over the Internet.

Method 810 is initiated at step 812 with the request for documentation for verifying identity. In accordance with the invention it is preferred that the identification information include a scanable code, such as a bar code, although alternatively or in addition one may use alphanumeric identification information and employ an OCR recognition method. At step 814, such information is sent to a publically accessible database, where the individual is checked at step 816 for possible problems if he is found in the database, or added to the database if he is not already there.

At step 818 the individual is assigned a cutaneous information device code by the central server for the system and the cutaneous information device code is stored in a database accessible over the Internet at step 820. The cutaneous information device or badge is printed at step 822 and applied to the individual at step 824. Information associated with the newly created cutaneous information device code is communicated to a location database at step 826. The cutaneous information device is then scanned at step 828 which both functions to test the functionality of the cutaneous information device and report the individual's entering into the controlled area of the air terminal, allowing permanent databasing of the location of the individual for future tracking and use, as well as for testing at step 830 of the likelihood of a threat at a future point in time. For example if two individuals known to have a connection enter into an air terminal, and only one enters an aircraft, that aircraft could be recalled and the individuals questioned to avoid a potential in-flight incident. As alluded to above, all parts of the inventive system may optionally communicate with each other using the Internet via cyberspace 832, for example the Internet.

For example, when an individual enters the controlled area of an air terminal access may be gained only through a turnstile actuated to allow passage of the individual by the scanning of the cutaneous information device on the individual at step 834 and successful passing of an electronic security check at step 830. Such security check may involve numerous diverse items of information, such as the purchaser of the airline ticket, previous travel and location information, and so forth, as well as, of course, security data collected by other systems and agencies.

When the individual enters the ramp to the aircraft at step 836, which is detected by scanning at a turnstile at step 836, the location is reported at step 836, databased at step 826 and tested at step 830. Databasing at step 826 and testing at step 830 are repeated at step 838 upon scanning of the cutaneous information device (badge) on entry into the aircraft, at step 840 on debarking the aircraft, at step 842 on entering the terminal and upon exiting the controlled area of the air terminal at step 844.

In accordance with the invention it is contemplated that an airline flight may be associated with another databased activity, such as a resort stay. In this case, the cutaneous information device may function to speed up the check in process discussed in connection with the embodiment of FIGS. 1-14 which may be the second phase of the method of FIG. 15. Accordingly, upon entry to the resort, the cutaneous information device on the individual is recognized at step 846 and also recognized and tested at step 848 upon entry into the pool area, and also utilized to implement resort specific processes as described in connection with the embodiment of FIGS. 1-14. In the event that testing indicates a problem at any point, the same is reported to the authorities at step 850.

Figure 16:
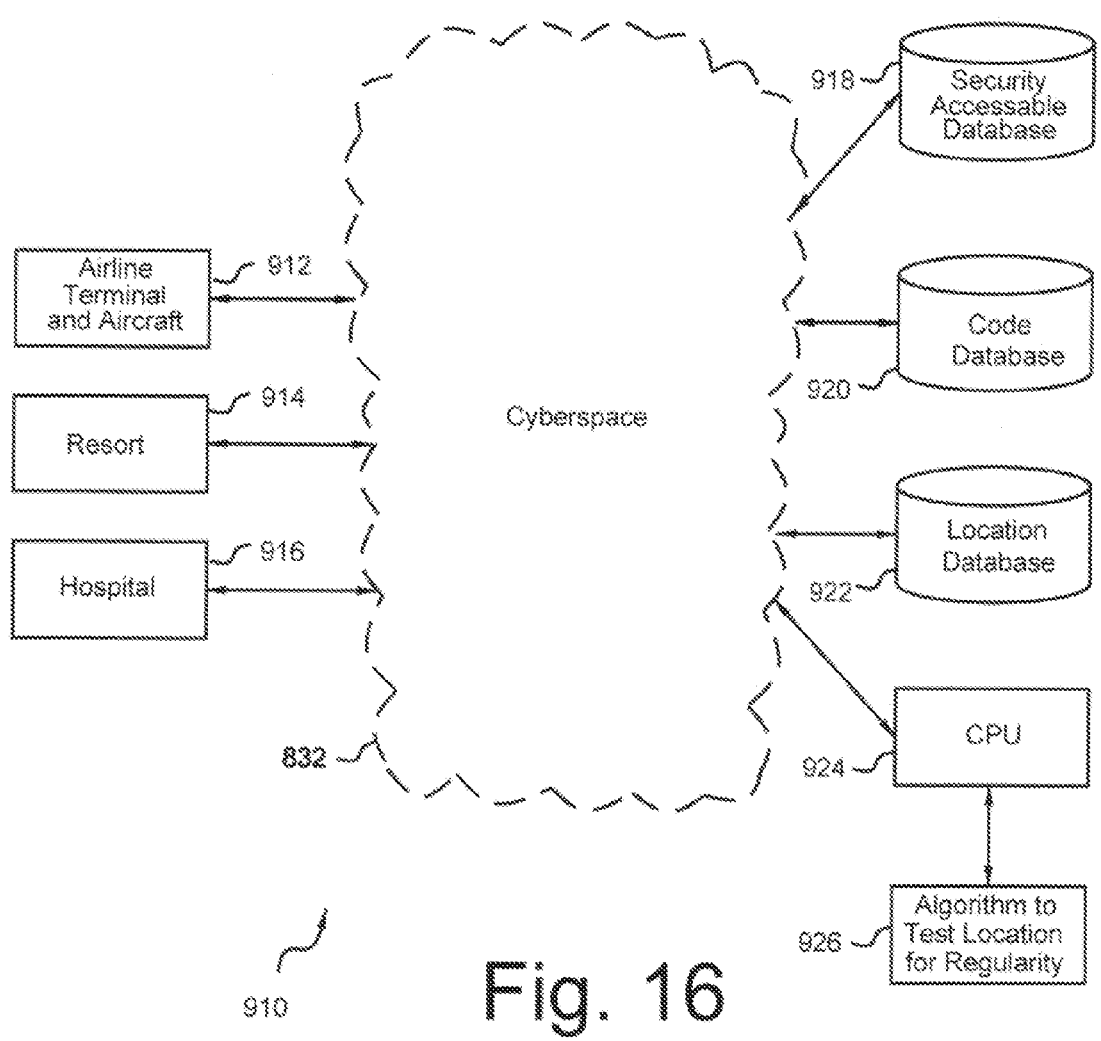
FIG. 16 illustrates a system for implementing the method of FIG. 15.

Referring to FIG. 16, it may be seen that a system 910 implementing the present invention comprises airline terminal and aircraft infrastructure subsystems 912, a resort infrastructure subsystem 914, and a hotel infrastructure subsystem 916, each of which communicates via cyberspace 832, for example, the Internet (or any other network), with security accessible database 918, code database 920, and location database 922. Such communication may be direct, or though a server 924. All parts of the system are in communication with server CPU 924, which in accordance with the preferred embodiment, determines the existence of possible threats, sends messages to various parts of the inventive system 910 to alert personnel and or the authorities based upon calculations made using collected data operated upon by an algorithm 926 stored on, for example, a solid state hard drive or hard drives.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. Apparatus for application to an individual's skin used for identifying and providing for the retrieval of information relating to the individual, comprising:
   (a) an adhesive layer;
   (b) a machine readable device secured to said adhesive layer, said machine readable device being encoded with identification information; and
   (c) a first quantity of ink deposited on said adhesive layer and arranged to provide a physiologically perceptible and humanly understandable visual indication of information relating to the individual, said adhesive layer, said machine readable device and said first quantity of ink forming a temporary cutaneous individual identification device, wherein the machine readable device and the first quantity of ink are secured to the individual's skin by the adhesive layer, whereby said individual identification device will deteriorate as the adhesive deteriorates.

2. The device as in claim 1, wherein the machine readable device secured to said adhesive layer comprises a second quantity of ink deposited on said adhesive layer and arranged to provide a machine readable image.

3. A plurality of devices as in claim 2, disposed on a carrier sheet.

4. The device as in claim 1, wherein the machine readable device secured to said adhesive layer comprises an RFID device deposited on said adhesive layer and arranged to provide a machine identification.

5. A plurality of devices as in claim 1, further comprising a quantity of image ink disposed on said adhesive layer and arranged to form a visual image of said individual.

6. The device as in claim 1, wherein said adhesive layer carries background ink arranged to enhance identification.

7. Apparatus as in claim 1, wherein said adhesive layer carries a glow in the dark phosphor.

8. A system comprising a plurality of individual identification devices as in claim 1, and further comprising:
   (d) a plurality of reader devices;
   (e) a computer interface device receiving information from said individual identification devices through said reader devices, and from said reader devices respecting the individuals identified by said individual identification devices;
   (f) a computer system coupled to said computer interface device, said computer system including a memory with an algorithm for processing said information respecting the individuals identified by said individual identification devices collected by said computer system.

9. Apparatus as in claim 8, wherein said algorithm is an artificial intelligence algorithm resident in said memory for assessing the likelihood of a dangerous situation.

10. Apparatus as in claim 8 further comprising software resident on said computer system for sending to said mobile devices or other devices reminders and/or alarms in response to the need to take particular actions or to notify users of a condition or situation, such as a dangerous condition, or to act as an alarm.

11. Apparatus as in claim 8, wherein said reader devices comprise fixed and mobile devices.

12. Apparatus as in claim 8, wherein a plurality of facilities, each comprising a separate set of reader devices and a separate service rendering apparatus, each output information from their respective reader devices to a common database, the contents of said common database being coupled to a computing device which communicates information to said plurality of facilities.

13. Apparatus as in claim 12, wherein said facilities comprise an airline terminal and a destination venue such as a hotel, resort or amusement park.

14. Apparatus as in claim 8, further comprising software resident on said computer system for sending to said mobile devices or other devices reminders and/or alarms in response to the need to take particular actions or to notify users of a condition or situation, such as a dangerous condition, or to act as an alarm, wherein said algorithm is an artificial intelligence algorithm resident in said memory for assessing the likelihood of a dangerous situation, and wherein said reader devices include mobile and fixed devices.

15. The device as in claim 1, wherein said adhesive layer carries background ink arranged to enhance identification and provide a visual cue to serve as a comparison mechanism between devices to insure proper identification of a device for application to said individual.

16. Apparatus as in claim 1, wherein said machine readable device is formed by printing said machine readable device on a support member coated with a release agent.

17. Apparatus as in claim 1 wherein the temporary cutaneous individual identification device is printed on paper carrying a water soluble release coating.

18. Apparatus as in claim 1, wherein said adhesive layer comprises contrasting background ink.

19. A device according claim 1 wherein the device further comprises a protective layer.

20. A system for associating an individual with information related to said individual, comprising:
   (a) a handheld apparatus for receiving identification information relating to an individual who is to receive a service;
   (b) an algorithm generating an identifier associated with said individual;
   (c) a storage device for storing said identifier;
   (d) a printer; and
   (e) a program resident in the memory of a computer, said computer communicating with said handheld apparatus, said program containing a set of instructions for generating a temporary cutaneous identification device by depositing ink in a configuration representing the individual's identification and at least a portion of information associated with the individual wherein said temporary cutaneous identification device is to be applied to the individual's skin with an adhesive, whereby said individual identification device will deteriorate as the adhesive deteriorates.

21. The system of claim 20, wherein said ink in a configuration representing identification is formed into a machine readable device and further formed into a physiologically perceptible and humanly understandable visual indication of information relating to the individual.

22. The system of claim 20, wherein said ink in a configuration representing identification is formed into a machine readable device containing information relating to the individual.

* * * * *